United States Patent

Braun et al.

Patent Number: 5,972,044
Date of Patent: Oct. 26, 1999

[54] COMPOSITION AND METHOD FOR DYEING KERATIN FIBERS

[75] Inventors: Hans-Juergen Braun, Ueberstorf; Pascal Andre Semadeni, Cordast, both of Switzerland

[73] Assignee: Wella AG, Darmstadt, Germany

[21] Appl. No.: 09/046,152

[22] Filed: Mar. 23, 1998

[30] Foreign Application Priority Data

Mar. 26, 1997 [DE] Germany .................. 197 12 649

[51] Int. Cl.$^6$ .................. A61K 7/13; D06P 1/90
[52] U.S. Cl. .................. 8/405; 8/565; 8/567; 8/568; 8/576; 8/603; 8/607
[58] Field of Search .................. 8/405, 414, 415, 8/424, 603, 607, 611, 407, 565, 567, 568, 576

[56] References Cited

U.S. PATENT DOCUMENTS

| 5,131,912 | 7/1992 | Ehara et al. .................. 8/405 |
| 5,558,677 | 9/1996 | Wagenmann et al. .................. 8/607 |

FOREIGN PATENT DOCUMENTS

| 43 35 626 A1 | 4/1995 | Germany . |
| 1-311012 | 12/1989 | Japan . |
| 3-058914 | 3/1991 | Japan . |

OTHER PUBLICATIONS

English language Abstract of DE 4,335,626, Henkle, Apr. 1995.

Fatiadi, "Pseudooxocarbons," Journal of Organic Chemistry, pp. 1338–1339, 1980 (no month available).

Primary Examiner—Caroline D. Liott
Attorney, Agent, or Firm—Michael J. Striker

[57] ABSTRACT

An aqueous or aqueous-alcoholic composition for dyeing natural or synthetic fibers, especially hair, contains a combination of at least one cyclic oxo-substituted enediol according to formula I:

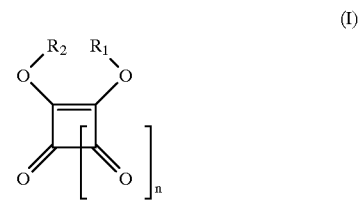

wherein $R_1$ and $R_2$ are the same or different and independently of each other represent a hydrogen atom or an alkali metal atom, or $R_1$ and $R_2$ together represent an alkaline earth metal atom and n=0, 1, 2 or 3; and at least one member selected from the group consisting of malonic acid dinitrile, maleic acid diaminodinitrile, 2,5-diamino-6-nitropyridine, 1,2,3,4-tetrahydro-6-nitroquinoxaline, 7-amino-3,4-dihydro-6-nitro-2H-1,4-benzoxazine and substituted nitrobenzene compounds; as well as water and at least one cosmetic ingredient including solvents other than water, surfactants, thickeners, care materials and adjuvant materials.

14 Claims, No Drawings

COMPOSITION AND METHOD FOR DYEING KERATIN FIBERS

BACKGROUND OF THE INVENTION

The present invention relates to a composition for dyeing natural or synthetic fibers containing cyclic oxo-substituted enediols, acid dinitrile, maleic acid diaminodinitrile or nitrobenzene derivative compounds and a method of dyeing of keratin fibers using this composition.

Dye systems based on oxo-substituted enediols are known from German Published Patent Application DE-OS 43 35 626. According to DE-OS 43 35 626 these compounds in combination with a primary or secondary amine group or a heterocyclic compound containing one nitrogen atom or an aromatic hydroxy compound, produce especially brilliant colors in the yellow, brown, green and violet ranges. Both reactive components are mixed with each other, heated to boiling and the cooled dye solution is filtered. This method is complicated and without heating produces a barely satisfactory orange shade or tone.

SUMMARY OF THE INVENTION

It is an object of the present invention to provide a composition for dyeing keratin fibers, especially human hair, and a method for keratin fibers using that composition which avoids the above-described disadvantages.

It is another object of the present invention to provide a composition for dyeing keratin fibers, especially human hair, and a method for dyeing the keratin fibers using it, which produces intense colors in a simple manner.

It has been surprisingly found that these objects can be attained using a combination of cyclic oxo-substituted enediols according to the formula I hereinbelow with malonic acid dinitrile, maleic acid diaminodinitrile, 2,5-diamino-6-nitropyridine, 1,2,3,4-tetrahydro-6-nitroquinoxaline, 7-amino-3,4-dihydro-6-nitro-2H-1,4-benzoxazine and/or substituted nitrobenzene compounds and the above-described disadvantages avoided in this way.

According to the invention, a composition for dyeing natural or synthetic fibers, especially keratin fibers, such as wool, fur or human hair, contains a combination of at least one cyclic oxo-substituted enediol according to formula I:

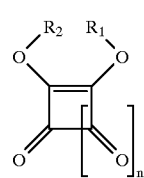

(I)

wherein $R_1$ and $R_2$ are the same or different and independently of each other represent a hydrogen atom or an alkali metal atom, or $R_1$ and $R_2$ together represent an alkaline earth metal atom and n=0, 1, 2 or 3;

and at least one ingredient selected from the group consisting of malonic acid dinitrile, maleic acid diaminodinitrile, 2,5-diamino-6-nitropyridine, 1,2,3,4-tetrahydro-6-nitroquinoxaline, 7-amino-3,4-dihydro-6-nitro-2H-1,4-benzoxazine and substituted nitrobenzene compounds.

Preferred cyclic oxo-substituted enediols according to formula (I) include those with n=2 or 3, namely dihydroxytrioxocyclopentene(croconic acid), dihydroxytetraoxocyclohexene (rhodizonic acid) and their alkali metal or alkaline earth metal salts.

The composition according to the invention preferably contains from 0.01 to 10 percent by weight, particularly from 0.1 to 5 percent by weight, of the cyclic oxo-substituted enediols of formula I.

The cyclic oxo-substituted enediols according to formula I produce intense and fashionable brown shades, red shades and black shades in combination with at least one ingredient selected from the group consisting of malonic acid dinitrile, maleic acid diaminodinitrile, 2,5-diamino-6-nitropyridine, 1,2,3,4-tetrahydro-6-nitroquinoxaline, 7-amino-3,4-dihydro-6-nitro-2H-1,4-benzoxazine and nitrobenzene derivative or substituted nitrobenzene compounds. The composition according to the invention includes a total amount of from 0.01 to 10 percent by weight, especially from 0.1 to 5 percent by weight, of the at least one ingredient selected from the group consisting of malonic acid dinitrile, maleic acid diaminodinitrile, 2,5-diamino-6-nitropyridine, 1,2,3,4-tetrahydro-6-nitroquinoxaline, 7-amino-3,4-dihydro-6-nitro-2H-1,4-benzoxazine and substituted nitrobenzene or nitrobenzene derivative compounds.

The at least one ingredient for use in the composition according to the invention can include, for example: 1,4-bis-[(2'-hydroxyethyl)amino]-2-nitrobenzene, 1-(2'-hydroxyethyl)amino-2-nitro-4-bis-(2"-hydroxyethyl)-aminobenzene (HC Blue no. 2), 1-amino-3-methyl-4-(2'-hydroxyethyl)amino-6-nitrobenzene (HC Violet no. 1), 4,N-ethyl,N-(2"-hydroxyethyl)amino-1-(2"-hydroxyethyl) amino-2-nitrobenzene hydrochloride (HC Blue no. 12), 4-bis-(2'-hydroxyethyl)amino-1-(2"-methoxyethyl)amino-2-nitrobenzene (HC Blue no. 11), 1-(2',3'-dihydroxypropyl)amino-2-nitro-4-[N-methyl-(2"-hydroxyethyl)amino] benzene hydrochloride (HC Blue no. 10), 1-[(2',3'-dihydroxypropyl)amino]-2-nitro-4-[N-ethyl-2"-(hydroxyethyl)amino]benzene hydrochloride (HC Blue no. 9), 1-(3'-hydroxypropylamino)-2-nitro-4-bis-(2"-hydroxyethylamino)benzene (HC Violet no. 2), 4,N-methyl, N-(2',3'-dihydroxypropyl)amino-1-methylamino-2-nitrobenzene hydrochloride (HC Blue no. 6), 4'-amino-2'-nitro-2"-carboxy-4"-dimethylamino-diphenylamine (HC Blue no. 13), 1-amino-4-(2'-hydroxyethyl)amino-2-nitrobenzene (HC Red no. 7), 4-amino-2-nitrodiphenyl-amine (HC Red no. 1),1-amino-2-nitro-4-bis-(2'-hydroxyethyl)aminobenzene hydrochloride (HC Red no. 13), 1-amino-2-nitro-4-(2'-hydroxyethyl)amino-5-chlorobenzene, 1-(2'-hydroxyethyl)amino-2-nitro-4-aminobenzene (HC Red no. 3), 1-hydroxy-3-nitro-4-aminobenzene, 1-hydroxy-3-nitro-4-(2'-hydroxyethylamino)benzene, 1-(2'-aminoethyl)-amino-2-nitro-4-(2'-hydroxyethoxy)benzene (HC Orange no. 2), 3-nitro-4-(2'-hydroxyethyl)aminophenylglyceryl ether (HC Orange no. 3), 1-amino-5-chloro-4-(2',3'-dihydroxypropyl)-amino-2-nitrobenzene (HC Red no. 10), 1,4-bis-[(2',3'-dihydroxypropyl)amino]-5-chloro-2-nitrobenzene (HC Red no. 11), 1-hydroxy-2-(2'-hydroxyethyl)amino-4,6-dinitrobenzene, 3-nitro-4-ethylaminobenzoic acid, 4-amino-2-nitrodiphenyl-amino-2-carboxylic acid, 2-chloro-6-ethylamino-4-nitrophenol, 2-amino-6-chloro-4-nitrophenol, 1-hydroxy-3-nitro-4-(3'-hydroxypropylamino)benzene, 2,5-diamino-6-nitro-pyridine, 1,2,3,4-tetrahydro-6-nitroquinoxaline, 7-amino-3,4-dihydro-6-nitro-2H-1,4-benzoxazine (HC Red 14), 1-amino-2-(2'-hydroxyethyl) amino-5-nitrobenzene (HC Yellow no. 5), 1-(2'-hydroxyethoxy)-2-(2"-hydroxyethyl)amino-5-nitrobenzene (HC Yellow no. 4), 1-(2'-hydroxyethyl)amino-2-nitrobenzene (HC Yellow no. 2), 1-methoxy-2-(2'- hydroxyethyl)-amino-5-nitrobenzene, 1-hydroxy-2-amino-3-nitrobenzene, 1-amino-2-methyl-6-nitrobenzene, 1-(2'-hydroxyethyl)-oxy-3-methylamino-4-nitrobenzene, 1-methylamino-2-nitro-5-(2',3'-dihydroxypropyl) oxybenzene, 1-(2'-hydroxyethyl)-amino-2-hydroxy-4-nitrobenzene (HC Yellow no. 11), 1-methoxy-3-(2'-aminoethyl)-amino-4-nitrobenzene hydrochloride (HC Yellow no.9), 1-(2'-ureidoethyl)amino-4-nitrobenzene, 4-(2',3'-dihydroxypropyl)amino-3-nitrotrifluoromethyl-benzene (HC Yellow no. 6), 2,4-bis-[N-(2'-hydroxyethyl) amino]-5-chloronitrobenzene (HC Yellow no. 10), 4-(2'-hydroxyethyl)-amino-3-nitromethylbenzene, 4-(2'-hydroxyethyl)amino-3-nitrochlorobenzene (HC Yellow no. 12), 4-(2'-hydroxyethyl)amino-3-nitrotrifluoromethylbenzene (HC Yellow no. 13), 4-(2'-hydroxyethyl) amino-3-nitrobenzonitrile (HC Yellow no. 14), 4-(2'-hydroxyethyl)amino-3-nitrobenzamide (HC Yellow no. 15) and especially nitroaniline derivates, for example 4-(di-(2-hydroxyethyl)amino)-2-nitroaniline, N-(2-hydroxyethyl)-4-methyl-2-nitroaniline,4-(2',3'-dihydroxypropyl)amino-3-nitrotrifluoromethylbenzene, 4-(2'-hydroxyethyl)amino-3-nitrochlorobenzene, 1-hydroxy-2-amino-4,6-dinitrobenzene and 4-(2'-hydroxyethyl)amino-3-nitromethylbenzene.

To obtain additional dye color tones or shades additional commonly used direct-dyeing dye compounds, such as azo dye compounds, anthraquinone dye compounds or triphenylmethane dye compounds, can be added alone or in a mixture with each other. For example, azo dye compound suitable for use in the composition of the invention include 1-(4'-nitrophenylazo)-2-methyl-4-bis-(2'-hydroxyethyl)-aminobenzene, 1-(3'-nitro-4-amino)phenylazo-2-hydroxy-7-trimethylammonium naphthalene chloride, 1-(2'-hydroxy-4'-sulfo-6'-nitro)naphthylazo-2-hydroxynaphthalene (C.I. 15700), 1-(4'-aminophenylazo)-2-methyl-4-bis-[(2'-hydroxyethyl)amino]benzene, 5-(4'-dimethylamino-phenylazo)-1,4-dimethyltriazonium chloride, 1-(2'-methoxyphenylazo)-2-hydroxy-7-trimethylmmonium naphthalene chloride, 1-(4'-aminophenylazo)-2-hydroxy-7-trimethylammonium naphthalene chloride, 4-(3'-trimethylammoniumphenylazo)-N-phenyl-3-methylpyrazolone(5) chloride, 4-hydroxy-3-[(4'-sulfo-1'-naphthyl)-azo]-1-naphthalene sulfonic acid, 1-(4'-sulfophenylazo)-2-hydroxynaphthalene,1-(4'-sulfonphenylazo)-2-hydroxy-6-sulfonaphthalene (C.I. 15985), 4-amino-[4'-bis-(2"-hydroxyethyl)amino] azobenzene, 4-amino-[4'-bis-(2"-hydroxy-ethyl)amino]-2'-methylazobenzene, 3-(2',6'-diaminopyridyl-3'-azo)pyridine, 7-phenylazo-1-amino-3,6-disulfo-8-hydroxy-naphthalene, 5-acetylamino-4-hydroxy-3-[(2'-methylphenyl)-azo]-2,7-naphthalene disulfonic acid and 2-(2',4'-dimethyl-phenylazo)-6-(4"-sulfophenylazo)-1,3-dihydroxybenzene.

Examples of anthraquinone dye compounds suitable for inclusion in the composition according to the invention include 1,4-bis-(2',3'-dihydroxypropyl)aminoanthraquinone, 1-methylamino-4-(2'-hydroxyethyl) aminoanthraquinone, 2-(2'-aminoethyl)amino anthraquinone, 2-bromo-4,8-diamino-6-(3'-trimethylammonium)-phenylamino-1,5-naphthoquinone chloride, 1-(2'-sulfo-4'-methylphenyl)-amino-4-hydroxyanthraquinone, 1,4-diaminoanthraquinone, 1-amino-2-sulfo-4-cyclohexyl-aminoanthraquinone, 1-methylamino-4-amino-propylamino-anthraquinone, 1-aminopropylamino-anthraquinone, 1,4-diamino-2-methoxyanthraquinone and 1,4-bis-(2-hydroxy-ethyl)-amino-5,8-dihydroxyanthraquinone.

Examples of suitable triphenylmethane dye compounds include 4',4",4"'-triamino-3-methyl-triphenylcarbonium chloride, bis-(4,4-diethylaminophenyl)-4'-ethylamino-naphthylcarbonium chloride, bis-(4,4-dimethylamino-phenyl)-4'-phenylamino-naphthylcarbonium chloride (Basic Blue 26, C.I. 44045) and 4,4-bis-(N-ethyl-3-sulfobenzyl) amino-2"-sulfofuchsonium chloride.

The total amount of the direct-dyeing dye additive compounds amounts to about 0.01 to 5 percent by weight, preferably from 0.1 to 4 percent by weight.

The dye composition according to the invention is basically suitable for dyeing natural fibers, such as keratin fibers (wool, fur, human hair), cotton, jute, sisal, linen or silk; modified natural fibers, such as regenerated cellulose, nitro cellulose, alkyl cellulose or hydroxy alkyl cellulose; and synthetic fibers, such as polyamide fibers or polyurethane fibers. The dye composition according to the invention is preferably used to dye keratin fibers, especially human hair.

The dye composition according to the invention can be in the form of an aqueous or aqueous-alcoholic solution, a cream, a gel, a surfactant-containing foaming solution (shampoo, aerosol) or an emulsion. It is composed of a mixture of the above-named dye compound ingredients with conventional cosmetic additive ingredients commonly used in this type of preparation.

Conventional cosmetic additive ingredients include, for example, solvents, such as water, lower aliphatic monovalent or polyvalent alcohols, their esters and ethers, for example alkanols, especially with one to four carbon atoms per molecule, for example ethanol, propanol, isopropanol, butanol or isobutanol, or divalent and trivalent alcohols, especially those with 2 to 6 carbon atoms per molecule, for example, ethylene glycol, propylene glycol, 1,3-propanediol, 1,4-butanediol, 1,5-pentanediol, 1,6-hexanediol, 1,2,6-hexanetriol, glycerol, diethyleneglycol or dipropyleneglycol, polyalkyleneglycols, such as triethylene glycol, polyethylene glycol, tripropylene glycol and polypropylene glycol, lower alkyl ethers of polyvalent alcohols, such as ethylene glycol monomethyl ether, ethyleneglycol monoethyl ether, diethylene glycol monomethyl ether, diethylene glycol monoethyl ether, triethylene glycol monomethyl ether or triethylene glycol monoethyl ether, ketones and ketoalcohols, especially those with 3 to 7 carbon atoms per molecule, such as acetone, methylethyl ketone, diethyl ketone, methylisobutyl ketone, methylphenyl ketone, cyclopentanone, cyclohexanone or diacetone alcohol; ethers, such as dibutyl ether, tetrahydrofuran, dioxane or diisopropyl ether; esters, such as ethyl formiate, methyl formiate, methyl acetate, ethyl acetate, propylene acetate, butyl acetate, phenyl acetate, ethylene glycol monoethyl ether acetate or acetic acid hydroxyethyl ester, amides, such as dimethylformamide, dimethylacetamide or N-methyl-pyrrolidone, urea, tetramethylurea and thiodiglycol. The dye composition according to the invention also can contain wetting agents and emulsifiers from the classes of anionic, cationic, amphoteric, nonionic or zwitterionic surface-active substances, for example fatty alcohol sulfates, alkane sulfonates, alkylbenzenesulfonates, alkyltrimethylammo-nium salts, alkylbetaines, α-olefin sulfonates, ethoxylated fatty alcohols, ethoxylated nonylphenols, fatty acid alkanol amines, ethoxylated fatty acid esters, fatty alcohol polyglycol ether sulfates or alkylpolyglucosides; thickeners, such as higher fatty alcohols, starches, cellulose derivative compounds, petrolatum (Vaseline®), paraffin oils or fatty acids and other fatty components in emulsified form, water-soluble polymeric thickener ingredients, such as natural gums, guar gum, xanthan gums, locust or carob bean extract, pectin, dextran, agar-agar, amylose, amyl pectin, dextrin or clay and completely synthetic hydrocolloids, such as polyvinyl alcohols; care materials, such as lanolin derivative compounds, cholesterol, pantothenic acids, water-soluble cationic polymers, protein derivative compounds, provitamins, vitamins, plant extracts, sugar or betaine; and adjuvant materials, such as electrolytes, antioxidants, fatty amides, sequestering agents, film-forming agents and preservatives.

The above-described conventional cosmetic additive ingredients are used in the dye composition according to the invention in amounts suitable for their purposes, for example the wetting agents and emulsifiers are used in a total amount of about 0.5 to 30 percent by weight, the thickeners in a total amount of about 0.1 to 25 percent by weight and the care ingredients in a total amount of about 0.1 to 5 percent by weight.

The composition according to the invention for dyeing keratin fibers has a pH of about 0.3 to 6.5. If the composition is used for the dyeing of human hair, the pH is preferably from 2 to 6.5. The adjustment of the pH occurs preferably with weak organic acids, such as citric acid, glycolic acid, lactic acid, malic acid, ascorbic acid or tartaric acid.

The dye composition according to the invention advantageously can be a 2-component preparation consisting of two separately packaged components. The two components are advantageously mixed immediately prior to use to form a ready-to-use dye mixture or composition. The ready-to-use dye mixture is made by mixing an aqueous or aqueous-alcoholic solution, which contains at least one compound from the group including malonic acid dinitrile, maleic acid diaminodinitrile and the nitrobenzene derivative compounds (component 1) with at least one cyclic oxo-substituted enediol according to formula I (component 2).

In the method of dyeing according to the invention a sufficient amount for dyeing of the hair, generally about 10 to 60 g, of the hair dye mixture or composition according to the invention is applied to the hair. This dye mixture is allowed to act on the hair for from about 10 to 60 minutes at 15 to 50° C., preferably about 20 to 45 minutes at 25 to 40° C., and then the hair is rinsed with water and dried. If necessary subsequently it is washed with a shampoo and/or with a weak organic acid, such as citric acid, glycolic acid, lactic acid, malic acid, ascorbic acid or tartaric acid. Subsequently the hair is dried.

The dye composition according to the invention already at temperatures under about 40° C. has a very good penetrating power on human hair and a very good coverage is provided from the hair roots to the hair tips. The hair dye compositions according to the invention provide a broad palette of different fashionable color shades from the red range to the brown and black range according to the type and composition of its ingredients. The comparatively great intensity and purity of the colors obtained are particularly noteworthy.

The subsequent examples should not be considered as limiting the subject matter of the invention claimed in the claims appended hereinbelow, although they are examples of the claimed invention.

EXAMPLES

Example 1

Hair Dye Composition with Potassium Rhodizonate 0.165 g malonic acid dinitrile
1.000 g isopropanol
0.100 g benzyl alcohol
0.500 g lactic acid
7.620 g water The above-described dye carrier mass is mixed directly prior to use with 0.615 g potassium rhodizonate to form the ready-to-use hair dyeing composition. The pH of this composition is 2.9. Bleached hair is then treated with this hair dye composition for 40 minutes at a temperature of 40° C. Subsequently the hair is rinsed with water and dried. The dyed hair is a cognac-brown color.

Example 2

Hair Dye Composition with Potassium Rhodizonate 0.270 g maleic acid diaminodinitrile
1.000 g isopropanol
0.100 g benzyl alcohol
0.500 g lactic acid
7.515 g water The above-described dye carrier mass is mixed directly prior to use with 0.615 g potassium rhodizonate to form the ready-to-use hair dyeing composition. The pH of this composition is 3.3. Bleached hair is then treated with this hair dye composition for 40 minutes at a temperature of 40° C. Subsequently the hair is rinsed with water and dried. The dyed hair is a red-brown color.

Example 3

Hair Dye Composition with Potassium Rhodizonate 0.603 g 4-(di(2-hydroxyethyl)amino)-2-nitroaniline
1.000 g isopropanol
0.100 g benzyl alcohol
0.500 g lactic acid
7.182 g water The above-described dye carrier mass is mixed directly prior to use with 0.615 g potassium rhodizonate to form the ready-to-use hair dyeing composition. The pH of this composition is 3.0. Bleached hair is then treated with this hair dye composition for 40 minutes at a temperature of 40° C. Subsequently the hair is rinsed with water and dried. The dyed hair is a dark violet-brown-black color.

Example 4

Hair Dye Composition with Croconic Acid 0.165 g malonic acid dinitrile
1.000 g isopropanol
0.100 g benzyl alcohol
0.500 g lactic acid
7.880 g water The above-described dye carrier mass is mixed directly prior to use with 0.355 g of croconic acid to form the ready-to-use hair dyeing composition. The pH of this composition is 0.3. Bleached hair is then treated with this hair dye composition for 40 minutes at a temperature of 40° C. Subsequently the hair is rinsed with water and dried. The dyed hair is a dark-brown-bordeaux red color.

Example 5

Hair Dye Composition with Croconic Acid 0.270 g maleic acid diaminodinitrile
1.000 g isopropanol
0.100 g benzyl alcohol
0.500 g lactic acid
7.775 g water The above-described dye carrier mass is mixed directly prior to use with 0.355 g croconic acid to form the ready-to-use hair dyeing composition. The pH of this composition is 0.4. Bleached hair is then treated with this hair dye composition for 40 minutes at a temperature of 40° C. Subsequently the hair is rinsed with water and dried. The dyed hair is a nut-brown color.

Example 6

Hair Dye Composition with Croconic Acid 0.603 g 4-(di(2-hydroxyethyl)amino)-2-nitroaniline
1.000 g isopropanol
0.100 g benzyl alcohol
0.500 g lactic acid
7.442 g water The above-described dye carrier mass is mixed directly prior to use with 0.355 g croconic acid to form the ready-to-use hair dyeing composition. The pH of this composition is 6.0. Bleached hair is then treated with this hair dye composition for 40 minutes at a temperature of 40° C. Subsequently the hair is rinsed with water and dried. The dyed hair is a reddish dark-brown color.

Example 7

Hair Dye Composition with Potassium Rhodizonate 0.245 g N-(2-hydroxyethyl)-4-methyl-2-nitroaniline
1.000 g isopropanol
0.100 g benzyl alcohol
0.500 g lactic acid
7.540 g water The above-described dye carrier mass is mixed directly prior to use with 0.615 g potassium rhodizonate to form the ready-to-use hair dyeing composition. The pH of this composition is 6.0. Bleached hair is then treated with this hair dye composition for 40 minutes at a temperature of 40° C. Subsequently the hair is rinsed with water and dried. The dyed hair is an intense orange color.

Example 8

Hair Dye Composition with Croconic Acid 0.245 g N-(2-hydroxyethyl)-4-methyl-2-nitroaniline
1.000 g isopropanol
0.100 g benzyl alcohol
0.500 g lactic acid
7.800 g water The above-described dye carrier mass is mixed directly prior to use with 0.355 g croconic acid to form the ready-to-use hair dyeing composition. The pH of this composition is 6.0. Bleached hair is then treated with this hair dye composition for 40 minutes at a temperature of 40° C. Subsequently the hair is rinsed with water and dried. The dyed hair is an orange color.

Example 9

Hair Dye Composition with Potassium Rhodizonate 0.892 g 1-((4-aminophenyl)azo)-7-(trimethylammonium)-2-naphthol
0.270 g maleic acid diaminodinitrile
1.000 g isopropanol
0.100 g benzyl alcohol
0.500 g lactic acid
6.623 g water The above-described dye carrier mass is mixed directly prior to use with 0.615 g potassium rhodizonate to form the ready-to-use hair dyeing composition. The pH of this composition is 2.7. Bleached hair is then treated with this hair dye composition for 40 minutes at a temperature of 40° C. Subsequently the hair is rinsed with water and dried. The dyed hair is a natural chestnut brown color.

Example 10

Hair Dye Composition with Croconic Acid 0.892 g 1-((4-aminophenyl)azo)-7-(trimethylammonium)-2-naphthol
0.270 g maleic acid diaminodinitrile
1.000 g isopropanol
0.100 g benzyl alcohol
0.500 g lactic acid
6.883 g water The above-described dye carrier mass is mixed directly prior to use with 0.355 g croconic acid to form the ready-to-use hair dyeing composition. The pH of this composition is 2.9. Bleached hair is then treated with this hair dye composition for 40 minutes at a temperature of 40° C. Subsequently the hair is rinsed with water and dried. The dyed hair is a natural chestnut brown color.

Example 11

Hair Dye Composition with Potassium Rhodizonate 0.596 g 1,4-diamino-9,10-anthracenedione
0.165 g malonic acid dinitrile
1.000 g isopropanol
0.100 g benzyl alcohol
0.500 g lactic acid
7.024 g water The above-described dye carrier mass is mixed directly prior to use with 0.615 g potassium rhodizonate to form the ready-to-use hair dyeing composition. The pH of this composition is 3.0. Bleached hair is then treated with this hair dye composition for 40 minutes at a temperature of 40° C. Subsequently the hair is rinsed with water and dried. The dyed hair is a red-brown color.

Example 12

Hair Dye Composition with Croconic Acid 0.596 g 1,4-diamino-9,10-anthracenedione
0.165 g malonic acid dinitrile
1.000 g isopropanol
0.100 g benzyl alcohol
0.500 g lactic acid
7.284 g water The above-described dye carrier mass is mixed directly prior to use with 0.355 g croconic acid to form the ready-to-use hair dyeing composition. The pH of this composition is 0.8. Bleached hair is then treated with this hair dye composition for 40 minutes at a temperature of 40° C. Subsequently the hair is rinsed with water and dried. The dyed hair is a fashionable, heavy red-brown color.

Example 13

Hair Dye Composition with Potassium Rhodizonate 1.284 g Di(4-(diethylamino)phenyl)(4-ethylamino)-naphthyl)carbenium chloride 0.270 g maleic acid diaminodinitrile
1.000 g isopropanol
0.100 g benzyl alcohol
0.500 g lactic acid
6.231 g water The above-described dye carrier mass is mixed directly prior to use with 0.615 g potassium rhodizonate to form the ready-to-use hair dyeing composition. The pH of this composition is 2.7. Bleached hair is then treated with this hair dye composition for 40 minutes at a temperature of 40° C. Subsequently the hair is rinsed with water and dried. The dyed hair is a dark blue grey color.

Example 14

Hair Dye Composition with Croconic Acid 1.284 g Di(4-(diethylamino)phenyl)(4-ethylamino)-naphthyl)carbenium chloride
0.270 g maleic acid diaminodinitrile
1.000 g isopropanol
0.100 g benzyl alcohol
0.500 g lactic acid
6.491 g water The above-described dye carrier mass is mixed directly prior to use with 0.355 g croconic acid to form the ready-to-use hair dyeing composition. The pH of this composition is 3.0. Bleached hair is then treated with this hair dye composition for 40 minutes at a temperature of 40° C. Subsequently the hair is rinsed with water and dried. The dyed hair is a olive green color.

Example 15

Hair Dye Composition with Potassium Rhodizonate 0.249 g 1-hydroxy-2-amino-4,6-dinitrobenzene
0.270 g maleic acid diaminodinitrile
1.000 g isopropanol
0.100 g benzyl alcohol
0.500 g lactic acid
7.266 g water The above-described dye carrier mass is mixed directly prior to use with 0.615 g potassium rhodizonate to form the ready-to-use hair dyeing composition. The pH of this composition is 3.4. Bleached hair is then treated with this hair dye composition for 40 minutes at a temperature of 40° C. Subsequently the hair is rinsed with water and dried. The dyed hair is a glistening natural reddish black color.

Example 16

Hair Dye Composition with Croconic Acid 0.249 g 1-hydroxy-2-amino-4,6-dinitrobenzene
0.165 g malonic acid dinitrile
1.000 g isopropanol
0.100 g benzyl alcohol
0.500 g lactic acid
7.631 g water The above-described dye carrier mass is mixed directly prior to use with 0.355 g croconic acid to form the ready-to-use hair dyeing composition. The pH of this composition is 0.7. Bleached hair is then treated with this hair dye composition for 40 minutes at a temperature of 40° C. Subsequently the hair is rinsed with water and dried. The dyed hair is a deep black color.

Example 17

Hair Dye Composition with Potassium Rhodizonate 0.197 g 4-((2-hydroxyethyl)amino)-2-nitroaniline
0.270 g maleic acid diaminodinitrile
1.000 g isopropanol
0.100 g benzyl alcohol
0.500 g lactic acid
7.318 g water The above-described dye carrier mass is mixed directly prior to use with 0.615 g potassium rhodizonate to form the ready-to-use hair dyeing composition. The pH of this composition is 3.5. Bleached hair is then treated with this hair dye composition for 40 minutes at a temperature of 40° C. Subsequently the hair is rinsed with water and dried. The dyed hair is a natural reddish-brown-black color.

Example 18

Hair Dye Composition with Croconic Acid 0.197 g 4-((2-hydroxyethyl)amino)-2-nitroaniline
0.165 g malonic acid dinitrile
1.000 g isopropanol
0.100 g benzyl alcohol
0.500 g lactic acid
7.683 g water The above-described dye carrier mass is mixed directly prior to use with 0.355 g croconic acid to form the ready-to-use hair dyeing composition. The pH of this composition is 1.5. Bleached hair is then treated with this hair dye composition for 40 minutes at a temperature of 40° C. Subsequently the hair is rinsed with water and dried. The dyed hair is a red-black color.

Example 19

Hair Dye Composition with Potassium Rhodizonate 0.357 g 4-(di(2-hydroxyethyl)amino)-N-(2-hydroxyethyl)-2-nitroaniline
0.270 g maleic acid diaminodinitrile
1.000 g isopropanol
0.100 g benzyl alcohol
0.500 g lactic acid
7.158 g water The above-described dye carrier mass is mixed directly prior to use with 0.615 g potassium rhodizonate to form the ready-to-use hair dyeing composition. The pH of this composition is 3.2. Bleached hair is then treated with this hair dye composition for 40 minutes at a temperature of 40° C. Subsequently the hair is rinsed with water and dried. The dyed hair is a natural glistening reddish deep black color.

Example 20

Hair Dye Composition with Croconic Acid 0.357 g 4-(di(2-hydroxyethyl)amino)-N-(2-hydroxyethyl)-2-nitroaniline
0.270 g maleic acid diaminodinitrile
1.000 g isopropanol
0.100 g benzyl alcohol
0.500 g lactic acid
7.418 g water The above-described dye carrier mass is mixed directly prior to use with 0.355 g croconic acid to form the ready-to-use hair dyeing composition. The pH of this composition is 1.0. Bleached hair is then treated with this hair dye composition for 40 minutes at a temperature of 40° C. Subsequently the hair is rinsed with water and dried. The dyed hair is a deep black color.

Unless otherwise indicated all percentages are percentages by weight.

While the invention has been illustrated and described as embodied in a composition and method for dyeing keratin fibers, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

We claim:

1. An aqueous or aqueous-alcoholic composition for dyeing natural or synthetic fibers, containing a combination of at least one cyclic oxo-substituted enediol according to formula I:

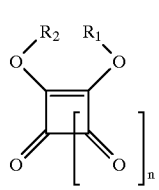

(I)

wherein $R_1$ and $R_2$ are the same or different and independently of each other represent a hydrogen atom or an alkali metal atom, or $R_1$ and $R_2$ together represent an alkaline earth metal atom and n=0, 1, 2 or 3;

at least one member selected from the group consisting of malonic acid dinitrile, maleic acid diaminodinitrile, 2,5-diamino-6-nitropyridine, 1,2,3,4-tetrahydro-6-nitroquinoxaline, 7-amino-3,4-dihydro-6-nitro-2H-1,4-benzoxazine and substituted nitrobenzene compounds; water; and at least one cosmetic ingredient selected from the group consisting of monovalent alcohols having one to four carbon atoms, divalent alcohols having two to six carbon atoms, trivalent alcohols having two to six carbon atoms, anionic surfactants, cationic surfactants, amphoteric surfactants, nonionic surfactants, zwitterionic surfactants, thickeners, care materials and adjuvant materials.

2. The aqueous or aqueous-alcoholic composition as defined in claim 1, wherein said at least one cyclic oxo-substituted enediol is dihydroxytrioxocyclopentene, dihydroxytetraoxocyclohexene and/or at least one alkali metal or alkaline earth metal salt thereof.

3. The aqueous or aqueous-alcoholic composition as defined in claim 1, containing from 0.01 to 10 percent by weight of said at least one cyclic oxo-substituted enediol.

4. The aqueous or aqueous-alcoholic composition as defined in claim 1, containing from 0.01 to 10 percent by weight of said at least one member selected from the group consisting of malonic acid dinitrile, maleic acid diaminodinitrile, 2,5-diamino-6-nitropyridine, 1,2,3,4-tetrahydro-6-nitroquinoxaline, 7-amino-3,4-dihydro-6-nitro-2H-1,4-benzoxazine and substituted nitrobenzene compounds.

5. The aqueous or aqueous-alcoholic composition as defined in claim 1, having a pH of from 0.3 to 6.5.

6. The aqueous or aqueous-alcoholic composition as defined in claim 5, further comprising an organic acid selected from the group consisting of citric acid, lactic acid, glycolic acid, malic acid, ascorbic acid and tartaric acid, and wherein said pH is from 2 to 6.5.

7. The aqueous or aqueous-alcoholic composition as defined in claim 1, further comprising at least one direct-dyeing dye compound selected from the group consisting of azo dye compounds, anthraquinone dye compounds and triphenylmethane dye compounds.

8. The aqueous or aqueous-alcoholic composition as defined in claim 1, wherein said substituted nitrobenzene compounds consist of 1,4-bis-[(2'-hydroxyethyl)amino]-2-nitrobenzene, 1-(2'-hydroxyethyl)-amino-2-nitro-4-bis-(2"-hydroxyethyl)-aminobenzene, 1-amino-3-methyl-4-(2'-hydroxyethyl)amino-6-nitrobenzene, 4,N-ethyl, N-(2"-hydroxyethyl)amino-1-(2"-hydroxyethyl)amino-2-nitrobenzene hydrochloride, 4-bis-(2'-hydroxyethyl)amino-1-(2"-methoxyethyl)amino-2-nitrobenzene, 1-(2',3'-dihydroxy-propyl)amino-2-nitro-4-[N-methyl-(2"-hydroxyethyl)amino]-benzene hydrochloride, 1-[(2',3'dihydroxypropyl)amino]-2-nitro-4-[N-ethyl-2"-(hydroxyethyl)amino]benzene hydro-chloride, 1-(3'-hydroxypropylamino)-2-nitro-4-bis-(2"-hydroxyethylamino)benzene, 4,N-methyl,N-(2',3'-dihydroxy-propyl)-amino-1-methylamino-2-nitrobenzene hydrochloride, 4'-amino-2'-nitro-2"-carboxy-4"-dimethylaminodiphenyl-amine, 1-amino-4-(2'-hydroxyethyl)amino-2-nitrobenzene, 4-amino-2-nitrodiphenylamine, 1-amino-2-nitro-4-bis-(2'-hydroxyethyl)-aminobenzene hydrochloride, 1-amino-2-nitro-4-(2'-hydroxyethyl)amino-5-chlorobenzene, 1-(2'-hydroxyethyl)amino-2-nitro-4-aminobenzene, 1-hydroxy-3-nitro-4-aminobenzene, 1-hydroxy-3-nitro-4-(2'-hydroxyethylamino)-benzene, 1-(2'-aminoethyl)amino-2-nitro-4-(2'-hydroxyethoxy)benzene, 3-nitro-4-(2'-hydroxyethyl)amino-phenylglyceryl ether, 1-amino-5-chloro-4-(2',3'-dihydroxy-propyl)-amino-2-nitrobenzene, 1,4-bis-[(2',3'-dihydroxypropyl)-amino]-5-chloro-2-nitrobenzene, 1-hydroxy-2-(2'-hydroxyethyl)amino-4,6-dinitrobenzene, 3-nitro-4-ethyl-aminobenzoic acid, 4-amino-2-nitrodiphenyl-amino-2-carboxylic acid, 2-chloro-6-ethyl-amino-4-nitrophenol, 2-amino-6-chloro-4-nitrophenol, 1-hydroxy-3-nitro-4-(3'-hydroxypropylamino) benzene, 1-amino-2-(2'-hydroxyethyl)-amino-5-nitrobenzene, 1-(2'-hydroxyethoxy)2-(2"-hydroxy-ethyl)amino-5-nitrobenzene, 1-(2'-hydroxyethyl)amino-2-nitrobenzene, 1-methoxy-2-(2'-hydroxyethyl)amino-5-nitrobenzene, 1-hydroxy-2-amino-3-nitrobenzene, 1-amino-2-methyl-6-nitrobenzene, 1-(2'-hydroxyethyl)oxy-3-methyl-amino-4-nitrobenzene, 1-methylamino-2-nitro-5(2',3'-dihydroxypropyl)oxybenzene, 1-(2'-hydroxyethyl)amino-2-hydroxy-4-nitrobenzene, 1-methoxy-3-(2'-aminoethyl) amino-4-nitrobenzene hydrochloride, 1-(2'-ureidoethyl) amino-4-nitrobenzene, 4-(2',3'-dihydroxypropyl)amino-3-nitro-trifluoromethylbenzene, 2,4-bis-[N-(2'-hydroxyethyl) amino]-5-chloronitrobenzene, 4-(2'-hydroxyethyl)amino-3-nitromethylbenzene, 4-(2'-hydroxyethyl)amino-3-nitrochlorobenzene, 4-(2'-hydroxyethyl)amino-3-nitrotrifluoromethylbenzene, 4-(2'-hydroxyethyl)amino-3-nitrobenzonitrile, 4-(2'-hydroxyethyl)amino-3-nitrobenzamide, 4-(di-(2-hydroxyethyl)amino)-2-nitroaniline, N-(2-hydroxyethyl)-4-methyl-2-nitroaniline, 4-(2',3'-dihydroxypropyl)amino-3-nitrotrifluoromethylbenzene, 4-(2'-hydroxyethyl)amino-3-nitrochlorobenzene, 1-hydroxy-2-amino-4,6-dinitrobenzene and 4-(2'-hydroxyethyl)-amino-3-nitromethylbenzene.

9. The aqueous or aqueous-alcoholic composition as defined in claim 1, in the form of a two component preparation consisting of a first component and a second component, wherein said second component includes said at least one cyclic oxo-substituted enediol and said first component includes said at least one member selected from the group consisting of malonic acid dinitrile, maleic acid diaminodinitrile, 2,5-diamino-6-nitropyridine, 1,2,3,4-tetrahydro-6-nitroquinoxaline, 7-amino-3,4-dihydro-6-nitro-2H-1,4-benzoxazine and substitute nitrobenzene compounds.

10. The aqueous or aqueous-alcoholic composition as defined in claim 1, consisting of a preparation for dyeing human hair.

11. A method of dyeing hair, said method comprising the steps of:
 a) providing a composition for dyeing hair;
 b) applying a sufficient amount of said composition for the dyeing of the hair to the hair;
 c) allowing said sufficient amount of said composition to act on the hair for from 10 to 60 minutes at 15 to 50° C.;
 d) rinsing the composition from the hair after step c) and washing with a shampoo if necessary; and
 e) drying the hair;
 wherein said composition for dyeing hair includes a combination of at least one cyclic oxo-substituted enediol according to formula I:

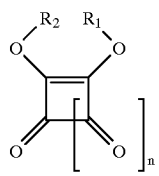

wherein $R_1$ and $R_2$ are the same or different and independently of each other represent a hydrogen atom or an alkali metal atom, or $R_1$ and $R_2$ together represent an alkaline earth metal atom and N=0, 1, 2 or 3;

at least one ingredient selected from the group consisting of malonic acid dinitrile, maleic acid diaminodinitrile, 2,5-diamino-6-nitropyridine, 1,2,3,4-tetrahydro-6-nitroquinoxaline, 7-amino-3,4-dihydro-6-nitro-2H-1,4-benzoxazine and substituted nitrobenzene compounds;

water; and at least one cosmetic ingredient selected from the group consisting of monovalent alcohols having one to four carbon atoms, divalent alcohols having two to six carbon atoms, trivalent alcohols having two to six carbon atoms, anionic surfactants, cationic surfactants, amphoteric surfactants, nonionic surfactants, zwitterionic surfactants, thickeners, care materials and adjuvant materials.

12. The method as defined in claim 11, wherein said at least one cyclic oxo-substituted enediol is dihydroxytrioxocyclopentene, dihydroxytetraoxocyclohexene and/or at least one alkali metal or alkaline earth metal salt thereof.

13. The method as defined in claim 11, wherein said composition contains from 0.01 to 10 percent by weight of said at least one cyclic oxo-substituted enediol.

14. The method as defined in claim 11, wherein said composition has a pH of from 2 to 6.5 and includes an organic acid added to adjust said pH.

* * * * *